US00PP31234P3

(12) United States Plant Patent
Hoogenraad

(10) Patent No.: US PP31,234 P3
(45) Date of Patent: Dec. 17, 2019

(54) ***PHYSOCARPUS* PLANT NAMED 'HOOGI031'**

(50) Latin Name: *Physocarpus opulifolius*
Varietal Denomination: Hoogi031

(71) Applicant: Mark Sebastiaan Hoogenraad, Ederveen (NL)

(72) Inventor: Mark Sebastiaan Hoogenraad, Ederveen (NL)

( * ) Notice: Subject to any disclaimer, the term of this patent is extended or adjusted under 35 U.S.C. 154(b) by 0 days.

(21) Appl. No.: 15/932,626

(22) Filed: Mar. 28, 2018

(65) Prior Publication Data

US 2019/0307037 P1 Oct. 3, 2019

(30) Foreign Application Priority Data

May 5, 2017 (QZ) ..... PBR 20171235

(51) Int. Cl.
*A01H 5/02* (2018.01)
*A01H 6/74* (2018.01)

(52) U.S. Cl.
USPC ..... Plt./226

(58) Field of Classification Search
USPC ..... Plt./226
CPC ..... A01H 5/02; A01H 5/00; A01H 6/74
See application file for complete search history.

(56) References Cited

PUBLICATIONS

Hoogenraad Catalogue 2017-2018, retrieved on Feb. 26, 2019, retrieved from the Internet at http://www.hoogenraadplant.nl/wp-content/uploads/2017/11/Catalogus2017-18ENG.pdf, pp. 1-2, 9, 28-30. (Year: 2018).*

Hoogenraad Stocklist 2017-2018, retrieved on Feb. 26, 2019, retrieved from the Internet at www.hoogenraadplant.nl/wp-content/uploads/2017/.../Stocklist-New-2017-2018.xls,2 pp. (Year: 2018).*

Plantipp *Physocarpus opulifolius* Little Breeny ('Hoogi031' PBR) EU 20171235, retrieved on Feb. 26, 2019, retrieved from the Internet at https://www.plantipp.eu/en/Plants/physocarpus-opulifolius-little-greeny-hoogi031pbr-2/, one page. (Year: 2019).*

* cited by examiner

*Primary Examiner* — June Hwu
(74) *Attorney, Agent, or Firm* — Penny J. Aguirre

(57) ABSTRACT

A new cultivar of *Physocarpus opulifolius* plant named, 'Hoogi031', that is characterized by its very compact plant habit, its foliage that is bright green in color, and its small sized leaves.

2 Drawing Sheets

CROSS REFERENCE TO RELATED APPLICATIONS

This application is related to U.S. Plant Patents for plants derived from the same breeding program that are entitled *Physocarpus* Plant Named 'Hoogi021' (U.S. Plant Pat. No. 27,986) and *Physocarpus* Plant Named 'Hoogi018' (U.S. Plant Pat. No. 28,059).

Botanical classification: *Physocarpus opulifolius.*

Varietal denomination: 'Hoogi031'.

BACKGROUND OF THE INVENTION

The present invention relates to a new and distinct cultivar of *Physocarpus opulifolius* and will be referred to hereafter by its cultivar name, 'Hoogi031'. 'Hoogi031' represents a new cultivar of *Physocarpus*, a deciduous shrub grown for landscape use.

The Inventor discovered the new cultivar in spring of 2014 as a naturally occurring branch mutation of *Physocarpus* 'Hoogi021' (U.S. Plant Pat. No. 27,986) that was growing in a container at his nursery in Ederveen, The Netherlands.

Asexual propagation of the new cultivar was first accomplished by stem cuttings by the Inventor in 2015 in Ederveen, The Netherlands. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Hoogi031' as a unique and distinct cultivar of *Physocarpus.*

1. 'Hoogi031' exhibits a very compact plant habit.
2. 'Hoogi031' exhibits foliage that is bright green in color.
3. 'Hoogi031' exhibits small sized leaves.

'Hoogi021', the parent plant of 'Hoogi031', is similar to 'Hoogi031' in plant height and in having leaves that are small in size. 'Hoogi021' differs from 'Hoogi031' in having foliage color that emerges brown-purple and matures to green suffused with black. 'Hoogi031' can also be compared to 'Hoogi018'. 'Hoogi018' is similar to 'Hoogi031' in having a very compact plant habit and in having small leaves. 'Hoogi018' differs from 'Hoogi031' in having foliage that is gray-purple-red in color.

BRIEF DESCRIPTION OF THE DRAWINGS

The accompanying colored photographs illustrate the overall appearance and distinct characteristics of the new

*Physocarpus*. The photographs were taken of a plant 8 months in age as grown outdoors in a 27-cm container in Ederveen, The Netherlands.

Figure 1:
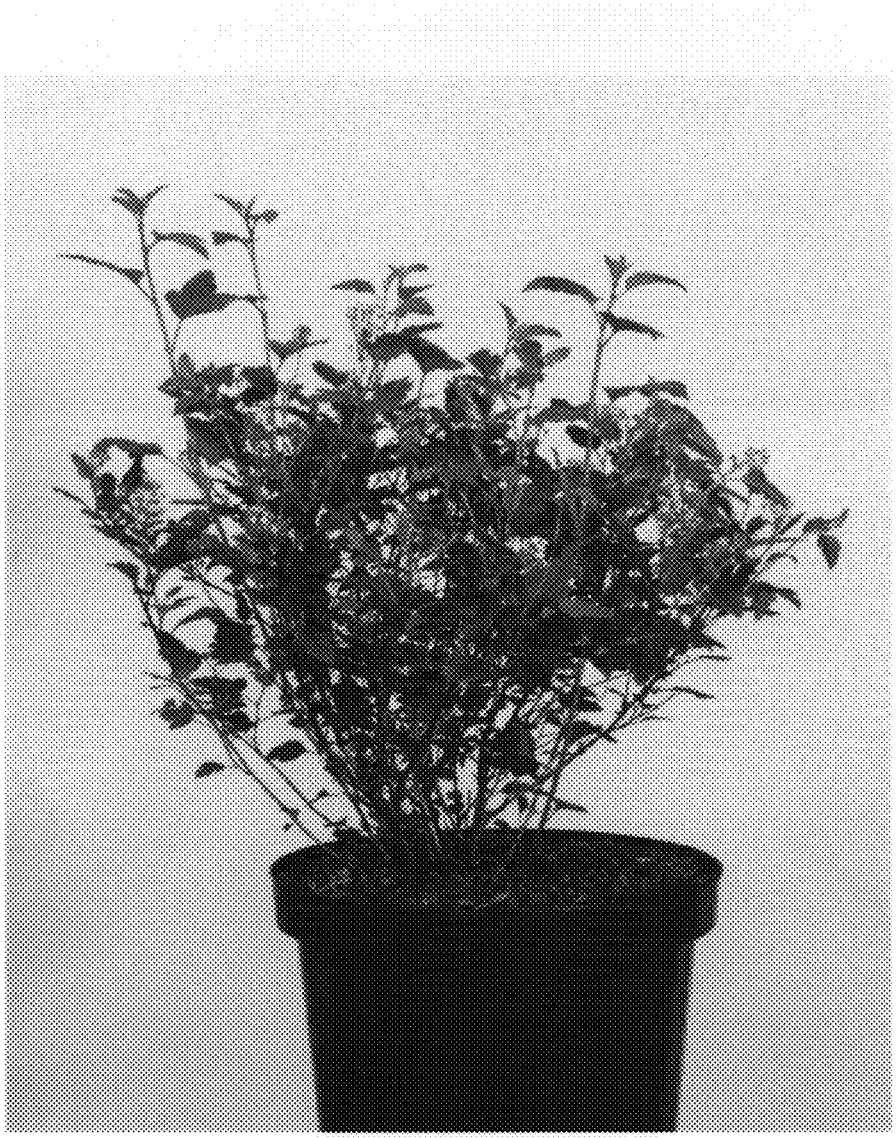

The photograph in FIG. 1 provides a side view of the plant in bloom of 'Hoogi031'.

Figure 2:
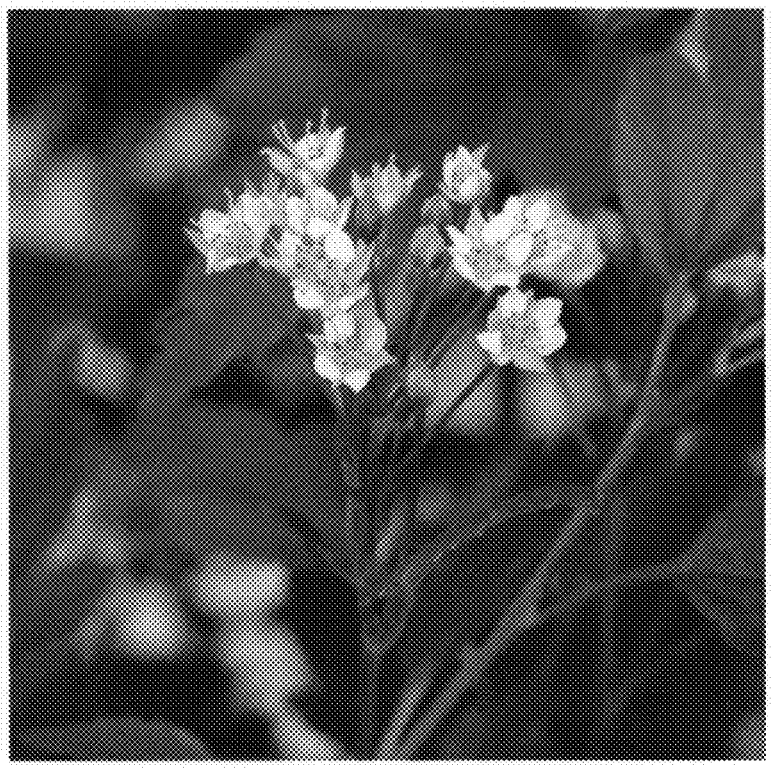

The photograph in FIG. 2 provides a close-up view of an inflorescence of 'Hoogi031'.

Figure 3:
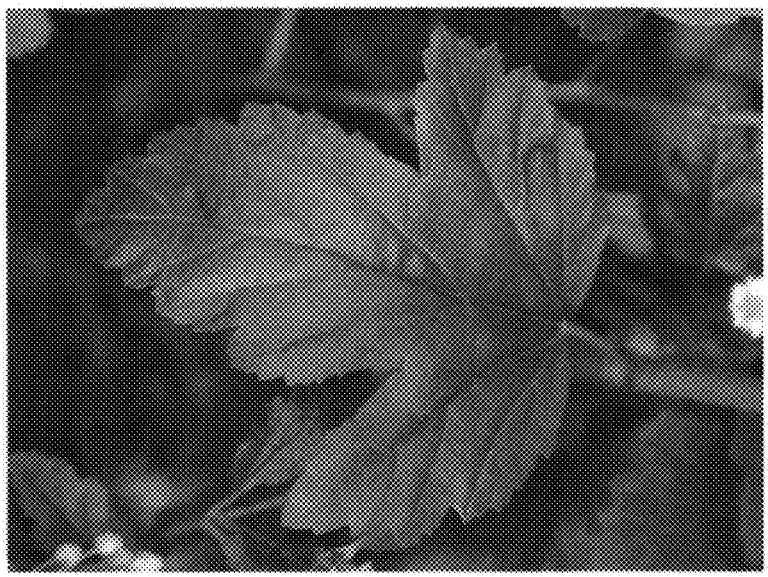

The photograph in FIG. 3 provides a close-up view of a leaf of 'Hoogi031'.

The colors in the photographs are as close as possible with the digital photography and printing techniques utilized and the color codes in the detailed botanical description accurately describe the colors of the new *Physocarpus*.

BOTANICAL DESCRIPTION OF THE PLANT

The following is a detailed description of 8-month-old plants of the new cultivar as grown outdoors in 27-cm containers in Ederveen, The Netherlands. Phenotypic differences may be observed with variations in environmental, climatic, and cultural conditions. The color determination is in accordance with The 2015 Colour Chart of The Royal Horticultural Society, London, England, except where general color terms of ordinary dictionary significance are used.

General Description:

*Blooming period.*—Late spring into summer in The Netherlands.

*Plant type.*—Deciduous shrub.

*Plant and growth habit.*—Upright, compact, freely branching.

*Height and spread.*—Reaches an average of 50 cm in height and 30 cm in spread as a four-year-old plant in the landscape.

*Hardiness.*—U.S.D.A. Zones 3 to 11.

*Diseases and pest resistance.*—No susceptibility and resistance to diseases or pests has been observed.

*Root description.*—Fibrous and fine.

*Growth rate.*—Low to moderately vigorous.

*Propagation.*—Softwood stem cuttings.

*Root development.*—An average of 2 weeks to initiate roots and about 12 months to produce a fully rooted plant in a 12-cm container.

Branch Description:

*Branch color.*—New wood; between 144A and 146B, mature branches and internodes; 200C to 200D, bark; between 199A and N200B, exfoliating.

*Branch size.*—An average of 19.4 cm in length and 3 mm in diameter.

*Stem aspect.*—Lateral branches are held in an average angle of 45° to main stems.

*Number of lateral branches.*—An average of 17 main branches, 29 lateral branches.

*Branch surface.*—Slightly glossy.

*Branch shape.*—Angular with 5 edges, older stems rounded.

*Branch internode length.*—An average 2.2 cm.

*Branch habit.*—Freely branching.

*Branch strength.*—Moderately strong.

Foliage Description:

*Leaf shape.*—Ovate, tri-lobed.

*Leaf division.*—Simple.

*Leaf base.*—Obtuse to very short attenuate.

*Leaf apex.*—Acute.

*Leaf venation.*—Pinnate, color; upper surface 146C, lower surface 138B.

*Leaf margin.*—Crenate.

*Leaf attachment.*—Petiolate.

*Leaf arrangement.*—Alternate.

*Leaf surface.*—Both surfaces smooth and glabrous, upper surface very slightly glossy, lower surface matte.

*Leaf size.*—An average of 6.6 cm in length and 5.3 cm in width.

*Leaf number.*—Average of 9 per lateral branch.

*Leaf color.*—Young foliage upper surface; 143A to 143B, young lower surface; 138A to 138B, mature foliage upper surface; 137A to 137B, mature lower surface; between 138A and 147B, fall color upper surface 137B with a slight flush of 164A, fall color lower surface; a color between 138A and 147A with a slight flush of 164B.

*Petiole.*—An average of 2.7 cm in length, 1.25 mm in diameter, upper surface slightly glossy, lower surface moderately glossy, moderate in strength, both surfaces 144B in color.

*Stipules.*—2 present at the proximal end of each petiole, leafy, obovate in shape, serrate margins, an average of 4 mm in length and 1 mm in width, color of both surfaces 143A.

Flower Description:

*Flower type.*—Small rotate flowers arranged in spherical corymbs.

*Flower fragrance.*—None.

*Flower lastingness.*—Average of one week, self-cleaning.

*Flower bud description.*—Ovate in shape, average of 4 mm in length and 2 mm in diameter, surface is smooth, glabrous and matte, 144A to 144B.

*Flower quantity.*—Average of 15 flowers per lateral stem, 550 per plant.

*Inflorescence size.*—Average of 4.6 cm in height and 2.7 cm in width.

*Flower size.*—Average of 6 mm in height, diameter and length.

*Peduncles.*—Average 3 cm in length and 1 mm in diameter, 144A in color, smooth and glabrous surface, moderately strong in strength, held straight on top of lateral branches (=0°).

*Pedicels.*—Average of 2.1 cm in length and 0.5 mm in diameter, 144B in color, smooth and glabrous surface, moderately strong in strength, held in an average of 25° to peduncle (=0°).

*Petal description.*—5, 1 whorl, broad ovate in shape, margin is entire, apex is short apiculate, lower and upper surfaces are matte, glabrous, velvety, base is cuneate, average of 3 mm in length and 2 mm in width, color; when opening and fully open upper and lower surfaces NN155D.

*Calyx size.*—Rotate, average of 4 mm in length and 6 mm in diameter.

*Sepal description.*—5, rotate, ovate and cup-shaped, margin is entire, apex is acute, broad cuneate base, an average of 4 mm in length and 1.5 mm in width, upper surface is matte, moderately covered with short pubescence average of 0.2 mm in length, lower surface is matte, glabrous and smooth, color; when opening and fully open upper surface 138D, when opening and fully open lower surface 144B.

Reproductive Organs:

*Gynoecium.*—Pistil; average of 5, average of 3.5 mm in length, stigma; club-shaped, 0.5 mm in length and diameter, 151D in color, style; average of 3 mm in length, 150D in color, ovary is 145C in color.

*Androecium.*—Stamens; average of 25, filaments; 2 mm in length, 157D in color, anthers; double kidney-shape, average of 0.3 mm in length and width, 159B to 159C in color, no pollen detected.

*Fruit and Seed.*—No fruit or seed detected to date.

It is claimed:

1. A new and distinct cultivar of *Physocarpus* plant named 'Hoogi031' substantially as herein illustrated and described.

* * * * *